United States Patent
Mehta

(10) Patent No.: US 6,977,163 B1
(45) Date of Patent: Dec. 20, 2005

(54) METHODS AND SYSTEMS FOR PERFORMING MULTIPLE REACTIONS BY INTERFACIAL MIXING

(75) Inventor: Tammy Burd Mehta, San Jose, CA (US)

(73) Assignee: Caliper Life Sciences, Inc., Mountain View, CA (US)

( * ) Notice: Subject to any disclaimer, the term of this patent is extended or adjusted under 35 U.S.C. 154(b) by 112 days.

(21) Appl. No.: 10/162,140

(22) Filed: Jun. 4, 2002

Related U.S. Application Data

(60) Provisional application No. 60/298,058, filed on Jun. 13, 2001.

(51) Int. Cl.⁷ .......................... C12Q 1/68; C12P 19/34; C07H 21/04
(52) U.S. Cl. .................. 435/91.2; 435/6; 436/501; 436/94; 536/23.1; 536/24.33
(58) Field of Search ................... 435/6, 91.1, 183; 536/23.1, 24.33; 204/456

(56) References Cited

U.S. PATENT DOCUMENTS

| | | | |
|---|---|---|---|
| 4,390,403 A | 6/1983 | Batchelder | |
| 4,908,112 A | 3/1990 | Pace | |
| 5,126,022 A | 6/1992 | Soane et al. | |
| 5,200,313 A * | 4/1993 | Carrico ........................ | 435/6 |
| 5,498,392 A | 3/1996 | Wilding et al. | |
| 5,525,494 A | 6/1996 | Newton | |
| 5,571,410 A | 11/1996 | Swedberg et al. | |
| 5,585,069 A | 12/1996 | Zanzucchi et al. | |
| 5,593,838 A | 1/1997 | Zanzucchi et al. | |
| 5,603,351 A | 2/1997 | Cherukuri et al. | |
| 5,635,358 A | 6/1997 | Wilding et al. | |
| 5,637,469 A | 6/1997 | Wilding et al. | |
| 5,699,157 A | 12/1997 | Parce | |
| 5,716,852 A | 2/1998 | Yager et al. | |
| 5,750,015 A | 5/1998 | Soane et al. | |
| 5,800,690 A | 9/1998 | Chow et al. | |
| 5,811,296 A * | 9/1998 | Chemelli et al. ........ | 435/287.2 |
| 5,858,187 A | 1/1999 | Ramsey et al. | |
| 5,858,195 A | 1/1999 | Ramsey | |
| 5,866,366 A | 2/1999 | Kallender | |
| 5,869,004 A | 2/1999 | Parce et al. | |
| 5,876,675 A | 3/1999 | Kennedy | |
| 5,880,071 A | 3/1999 | Parce et al. | |
| 5,882,465 A | 3/1999 | McReynolds | |
| 5,885,470 A | 3/1999 | Parce et al. | |
| 5,932,100 A | 8/1999 | Yager et al. | |
| 5,942,443 A | 8/1999 | Parce et al. | |
| 5,948,227 A | 9/1999 | Dubrow | |
| 5,955,028 A | 9/1999 | Chow | |

(Continued)

FOREIGN PATENT DOCUMENTS

WO    WO 9604547    2/1996

(Continued)

OTHER PUBLICATIONS

Allen et al., "Polymerase Chain Reaction Amplification Products Separat," Biotechniques, 1989, vol. 7, No. 7, pp. 736-744 (Abstract only).*

(Continued)

*Primary Examiner*—Bradley L. Sisson
(74) *Attorney, Agent, or Firm*—Donald R. McKenna; Ann C. Petersen

(57) ABSTRACT

Methods and systems of performing multiple reactions in a high throughput format by utilizing interfacial mixing of adjacently positioned reagent slugs in a fluid conduit. Preferred applications of the methods and systems are in performing biochemical analyses, including genotyping experiments for multiple different loci on multiple different patient samples. Microfluidic systems are provided that increase throughput, automation and integration of the overall reactions to be carried out.

11 Claims, 4 Drawing Sheets

U.S. PATENT DOCUMENTS

| | | |
|---|---|---|
| 5,958,694 A | 9/1999 | Nikiforov |
| 5,959,291 A | 9/1999 | Jensen |
| 5,965,410 A | 10/1999 | Chow et al. |
| 5,976,336 A | 11/1999 | Dubrow et al. |
| 5,989,402 A | 11/1999 | Chow et al. |
| 6,001,229 A | 12/1999 | Ramsey |
| 6,001,231 A | 12/1999 | Kopf-Sill |
| 6,007,775 A * | 12/1999 | Yager .......................... 422/57 |
| 6,012,902 A | 1/2000 | Parce |
| 6,042,709 A | 3/2000 | Parce et al. |
| 6,046,056 A * | 4/2000 | Parce et al. ............ 204/403.05 |
| 6,057,149 A * | 5/2000 | Burns et al. ............. 435/287.2 |
| 6,062,261 A | 5/2000 | Jacobson et al. |
| 6,074,725 A | 6/2000 | Kennedy |
| 6,090,552 A | 7/2000 | Nazarenko |
| 6,100,541 A | 8/2000 | Nagle et al. |
| 6,117,635 A | 9/2000 | Nazarenko |
| 6,120,666 A | 9/2000 | Jacobson et al. |
| 6,150,180 A * | 11/2000 | Parce et al. ................. 436/514 |
| 6,153,073 A * | 11/2000 | Dubrow et al. ............. 204/453 |
| 6,174,675 B1 | 1/2001 | Chow et al. |
| 6,221,226 B1 | 4/2001 | Kopf-Sill |
| 6,235,471 B1 | 5/2001 | Knapp et al. |
| 6,280,589 B1 | 8/2001 | Manz et al. |
| 6,451,530 B1 * | 9/2002 | Hawkins ........................ 435/6 |
| 6,632,641 B1 * | 10/2003 | Brennan et al. ........... 435/91.2 |
| 2002/0031836 A1 * | 3/2002 | Feldstein .................... 436/180 |
| 2002/0110828 A1 * | 8/2002 | Ferea et al. .................... 435/6 |

FOREIGN PATENT DOCUMENTS

| WO | WO 9702357 | 1/1997 |
|---|---|---|

OTHER PUBLICATIONS

Dasgupta, P.K. et al., "Electroosmosis: A Reliable Fluid Propulsion System for Flow Injection Analysis," *Anal. Chem.* (1994) 66:1792-1798.

Effenhauser, C.S. et al., "Glass Chips for High-Speed Capillary Electrophoresis Separations with Submicrometer Plate Heights," *Anal. Chem.* (1993) 65: 2637-2642.

Effenhauser, C.S. et al., "High Speed Separation of Anitsense Oligonucleotides on a Micromachined Capillary Electrophoresis Device," *Anal. Chem.* (1994) 66: 2949-2953.

Effenhauser, C.S., et al., "Integrated Capillary Electrophoresis on Flexible Silicone Microdevices: Analysis of DNA Restriction Fragments and Detection of Single DNA Molecules on Microchips," *Anal. Chem.* (1997) 69: 3451-3457.

Fan, Z.H. et al., "Micromachining of Capillary Electrophoresis Injectors and Separators on Glass Chips and Evaluation of Flow at Capillary Intersections," *Anal. Chem.* (1994) 66: 177-184.

Fister, J.C. III et al., "Counting Single Chromophore Molecules for Ultrasensitive Analysis and Separations on Microchip Devices," *Anal. Chem.* (1998) 70: 431-437.

Hadd, A.G. et al., "Microfluidic Assays of Acetylcholinesterase," *Anal. Chem.* (1999) 71: 5206-5212.

Harrison, J. et al., "Capillary Electrophoresis and Sample Injection Systems Integrated on a Planar Glass Chip," *Anal. Chem.* (1992) 64: 1926-1932.

Harrison, J. et al., "Towards Miniaturized Electrophoresis and Chemical Analysis Systems on Silicon: An Alternative to Chemical Sensors*," *Sensors and Actuators B* (1993) 10: 107-116.

Harrison, J. et al., "Micromachining a Miniaturized Capillary Electrophoresis-Based Chemical Analysis System on a Chip," *Science* (1993) 261: 895-897.

Harrison, D.J. et al., "Integrated Electrophoresis Systems for Biochemical Analyses," *Solid-State Sensor and Actuator Workshop* (1994) 21-24.

Jacobson, S.C. et al., "Effects of Injection Schemes and Column Geometry on the Performance of Microchip Electrophoresis Devices," *Anal. Chem.* (1994) 66:1107-1113.

Jacobson, S.C. et al., "High-Speed Separations on a Microchip," *Anal. Chem.* (1994) 66:1114-1118.

Jacobson, S.C. et al., "Open Channel Electrochromatography on a Microchip," *Anal. Chem.* (1994) 66: 2369-2373.

Jacobson, S.C. et al., "Precolumn Reactions with Electrophoretic Analysis Integrated on a Microchip," *Anal. Chem.* (1994) 66: 4127-4132.

Jacobson, S.C. et al., "Microchip Electrophoresis with Sample Stacking," *Electrophoresis* (1995) 16: 481-486.

Jacobson, S.C. et al., "Fused Quartz Substrates for Microchip Electrophoresis," *Anal. Chem.* (1995) 67: 2059-2063.

Jacobson, S.C. et al., "Integrated Microdevice for DNA Restriction Fragment Analysis," *Anal. Chem.* (1996) 68: 720-723.

Jacobson, S.C. et al., "Electrokinetic Focusing in Microfabricated Channel Structures," *Anal. Chem.* (1997) 69: 3212-3217.

Jacobson, S.C. et al., "Microfluidic Devices for Electrokinetically Driven Parallel and Serial Mixing," *Anal. Chem.* (1999) 71: 4455-4459.

Manz, A. et al., "Miniaturized Total Chemical Analysis Systems: a Novel Concept for Chemical Sensing," *Sensors and Actuators* (1990) B1: 244-248.

Manz, A. et al., "Micromachining of Monocrystallin Silicon and Glass for Chemical Analysis Systems," *Trends in Analytical Chemistry* (1991) 10:144-149.

Manz, A. et al., "Planar Chips Technology for Miniaturization and Integration of Separation Techniques into Monitoring Systems," *Journal of Chromatography* (1992) 593:253-258.

Manz, A. et al., "Planar Chips Technology for Miniaturization of Separation Systems: A Developing Perspective in Chemical Monitoring."

Manz, A. et al., "Electroosmotic Pumping and Electrophoretic Separations for Miniaturized Chemical Analysis Systems," J. Micromach. Microeng. (1994) 4: 257-265.

Manz, A. et al., "Parallel Capillaries for High Throughput in Electrophoretic Separations and Electroosmotic Drug Discovery Systems," International Conference on Solid-State Sensors and Actuators (1997) 915-918.

McCormick, R.M. et al., "Microchannel Electrophoretic Separations of DNA in Injection-Molded Plastic Substrates," *Anal. Chem.* (1997) 69: 2626-2630.

Moore, A.W. et al., "Microchip Separations of Neural Species via Micellar Electrokinetic Capillary Chromatography," *Anal. Chem.* (1995) 67: 4184-4189.

Ramsey, J.M. et al., "Microfabricated Chemical Measurement Systems," *Nature Medicine* (1995) 1:1093-1096.

Salimi-Moosavi, H. et al., "Biology Lab-on-a-Chip for Drug Screening," Solid-State Sensor and Actuator Workshop (1998) 350-353.

Seiler, K. et al., "Planar Glass Chips for Capillary Electrophoresis: Repetitive Sample Injection, Quantitation, and Separation Efficiency," *Anal. Chem.* (1993) 63:1481-1488.

Seiler, K. et al., "Electroosmotic Pumping and Valveless Control of Fluid Flow within a Manifold of Capillaries on a Glass Chip," *Anal. Chem.* (1994) 66:3485-3491.

Ueda, M. et al., "Imaging of a Band for DNA Fragment Migrating in Microchannel on Integrated Microchip," *Materials Science and Engineering C* (2000) 12:33-36.

Wang, C. et al., "Integration of Immobilized Trypsin Bead Beds for Protein Degestion within a Microfluidic Chip Incorporating Capillary Electrophoresis Separations and an Electrospray Mass Spectrometry Interface," *Rapid Commin. Mass Spectrom.* (2000) 14:1377-1383.

Woolley, A.T. et al., "Ultra-High-Speed DNA Fragment Separations Using Microfabricated Capillary Array Electrophoresis Chips," *Proc. Natl. Acad. Sci. USA* (1994) 91:11348-11352.

Woolley, A.T. et al., "Functional Integration of PCR Amplification and Capillary Electrophoresis in a Microfabricated DNA Analysis Device," Anal. Chem. (1996) 68: 4081-4086.

Woolley, A.T. et al., "High-Speed DNA Genotyping Using Microfabricated Capillary Array Electrophoresis Chips," *Anal. Chem.* (1977) 69:2181-2186.

Woolley, A.T. et al., "Capillary Electrophoresis Chips with Integrated Electrochemical Detection," *Anal. Chem.* (1998) 70: 684-688.

Zhang, B. et al., "Microfabricated Devices for Capillary Electrophoresis-Electrospray Mass Spectrometry," *Anal. Chem.* (1999) 71:3258-3264.

* cited by examiner

METHODS AND SYSTEMS FOR PERFORMING MULTIPLE REACTIONS BY INTERFACIAL MIXING

CROSS-REFERENCE TO RELATED APPLICATION

This application claims the benefit of U.S. Provisional Patent Application No. 60/298,058, filed Jun. 13, 2001, which is incorporated herein by reference in its entirety for all purposes.

BACKGROUND OF THE INVENTION

Higher throughput experimentation is a consistent goal for high-technology industries that depend upon research and development for growth, e.g., pharmaceutical, biotechnology and chemical industries. In the case of biological and chemical research, microfluidic technology has attempted to address this need by miniaturizing, automating and multiplexing experiments so that more experiments can be carried out faster and in a less expensive fashion. However, even these advances have highlighted the need and/or desire for even higher throughput experimentation within these industries. In particular, as with every other type of fluid based experimentation, microfluidic technology is limited by the fact that analyzing a given reaction requires mixing the reagents together in isolation and analyzing the results. Typically, such analysis has required a separate reaction vessel into which the different reagents must be pipetted. Higher throughput has then been achieved by increasing the number of reaction vessels, e.g., through the use of multiwell plate formats, increasing the complexity of pipetting systems, or in some rare cases, by carrying out multiple reactions in a single mixture. As can be readily appreciated, when one wishes to perform a matrixed experiment, e.g., testing each of a first library of reagents against each of a second library of experiments, the number of different reactions can potentially be staggering.

One example of such a matrixed experiment that is of considerable interest is that involved in genotyping experiments, e.g., SNP genotyping. In particular, it has been hypothesized that there is a correlation between the genetic footprint of a patient, e.g., as represented by the pattern of different genetic markers, e.g., SNPs, and that patient's response to different pharmaceutical treatments, susceptibility to disease, etc. In order to identify such a pattern, a large number of different patients need to be genotyped as to a large number of different genetic marker loci, in order to identify such correlations, so that they can be later used as diagnostic or therapeutic aids.

Microfluidic systems have addressed the throughput need for analytical operations, including genetic analysis, by providing very small fluidic channels coupled to an external fluid sipping element, e.g., a sampling capillary, through which reagents are drawn into the fluidic channel, where different reactions are carried out (See commonly owned U.S. Pat. No. 5,942,443). By serially drawing different samples into flowing reagent streams, such systems are capable of analyzing large numbers of different reactions in a relatively short amount of time. Further, by providing multiple parallel sipping and channel systems, one can further increase the number of experiments that are carried out.

While these systems have proven highly effective, each channel network has typically only been used to perform a single assay against a battery of test compounds or reagents. For example, in a particular channel, a given enzyme or target system is screened against a large number of potential inhibitors or test compounds. In the case of a matrixed experiment, e.g., screening a large number of enzymes or targets against a large number of potential inhibitors or test compounds, this particular operation would amount to one column of the matrix. Different columns of the matrix would be performed by other channel systems that are either within the same body or device, or are alternatively, completely separate. For example, one channel may be used to screen compounds for an effect on one enzyme system, while another channel in the same device, would be used to screen those compounds for an effect on a different enzyme system.

By way of example, in previously described operations, a first reagent is resident within the microfluidic device and is continuously introduced into the channels of the device. A large number of different second reagents are then serially introduced into the channel system to be reacted with (or interrogated against) the first reagent. Other reaction channel networks in the same device then optionally include different first reagents to perform other columns of the matrix. However, complexities of fixed sampling element positioning in microfluidic devices make such experiments difficult to configure, as different channel systems would not visit all of the same external sample sources, e.g., certain channels would not be able to access all of the test sample wells in a multiwell plate.

The present invention addresses the needs of higher throughput, matrixed experimentation, while taking advantage of the benefits of microfluidic technology in miniaturization, integration and automation.

SUMMARY OF THE INVENTION

The present invention generally provides methods and systems that utilize interfacial mixing of adjacent fluid plugs within a fluid conduit to perform multiple different analytical reactions. In at least one aspect, the invention provides a method of analyzing a plurality of reactions. The method comprises serially introducing plugs of first, second and third fluid borne reagents into a first fluid conduit under conditions suitable for performing the plurality of reactions whereby the plug of the first fluid borne reagent is abutted by the plug of the second fluid borne reagent at a first interface, and the plug of the second fluid borne reagent is abutted by the plug of the third fluid borne reagent at a second interface. The reagents are allowed a sufficient time for diffusion of effective amounts of the first and second reagents across the first interface whereupon the first and second reagents mix and react in a first reaction mixture, as well as sufficient time for diffusion of effective amounts of the second and third reagents across the second interface, whereupon the second and third reagents react in a second reaction. The results of the first and second reactions are then analyzed.

DETAILED DESCRIPTION OF THE INVENTION

Figure 1:
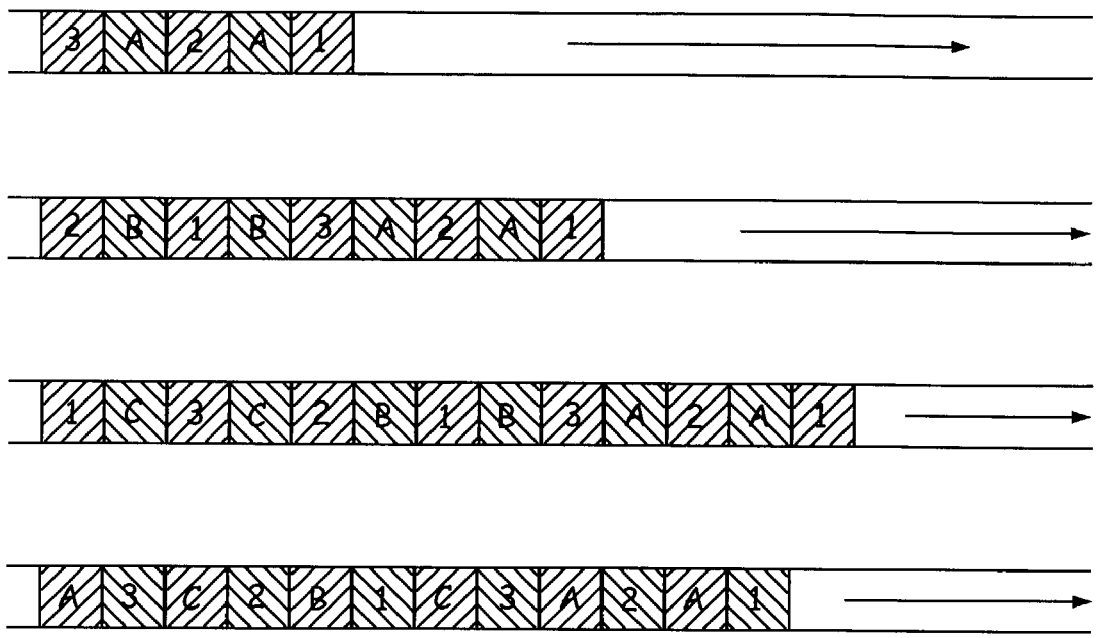
FIG. 1 schematically illustrates interfacial matrixed reactions in accordance with the present invention.

The present invention provides methods of rapidly performing a large number of reactions on one or more different materials of interest in a single fluidic system, and with extremely small quantities of reagents. The methods of the invention are particularly suited to performing matrixed experiments, e.g., experiments that are performed using a range of first reactants separately reacted with each of a range of second reactants. In particular, the present invention takes advantage of interfacial diffusion/dispersion in reagent plugs that are serially introduced into a fluid conduit to process, in series, different columns of the matrixed reaction. This is illustrated in FIG. 1 for a matrixed reaction of a library of first reagents A, B and C (shown as hatched slugs-///) against a library of second reagents 1, 2 and 3 (shown as hatched slugs-\\\). Although described with reference to three-member reagent libraries, it will be appreciated that each library will range in size from, e.g., about 5 different reagent members to up to thousands of reagent members, e.g., 10,000, 100,000 or more, and typically, from about 10 to about 5000 different reagent library members.

As shown in FIGS. 1A–C a conduit is provided. A reagent from the first reagent library, e.g., reagent A, is introduced as a plug into the conduit followed by a plug of first reagent from the second library, e.g., reagent 1 (FIG. 1A). Another plug of reagent A is then introduced into the conduit following and adjoining or abutting the plug of reagent 1. A plug of a second reagent from the second library, e.g., reagent 2, is introduced following and abutting reagent A. Again, a plug of reagent A follows reagent 2, which is in turn followed by reagent 3. Subsequent to, and optionally abutting reagent 3, a plug of a second reagent from the first library is introduced into the conduit. This is then followed by reagent 1, reagent B and reagent 2, and optionally reagent B followed by reagent 3 (although this is not necessary, as reagent B already abuts reagent 3). This is further repeated with reagent C. The resulting conduit (as shown in FIG. 1C) includes all of the various reagents of the first library abutting each of the reagents in the second library at one or more fluid interfaces.

In the conduit, each of the different reagent plugs then diffuses and/or disperses into the adjoining reagent slugs. In each of these resulting reaction mixtures, the reactions of interest are carried out, and the results are determined/measured and recorded as the material moves through the conduit past a detection point. As can be seen, a simple organization of reagent plugs dictates the reactions that occur. As is also apparent from FIG. 1, the organization of the fluid plugs can result in certain reactions being duplicated, which in some cases, may not be desirable, e.g., where maximum throughput is desired, and where there is a substantial number of duplicated reactions, e.g., where the number of reagents in each library are similar. In such cases, algorithms may be used which minimize the duplication of reactions. By way of example, in the simple illustration shown in FIGS. 1A–C, one could rearrange the order in which reagents are introduced in order to eliminate any duplicated interfaces. FIG. 1D illustrates just such an arrangement. As shown, reagent one is followed by reagent A which is followed by reagent 2. To avoid duplication of the 2+B interface, reagent B is then introduced followed by reagent 3, and reagent C. This is then followed by reagent 1, followed by reagent B and reagent 3, which is followed by reagent A. In this fashion, all possible combinations of interfaces have been represented with only one duplicated reaction, as opposed to 3 in the previous example. For other types of reactions, e.g., where a large number of different first reagents are screened against a small number of second reagents, the effect of duplications on throughput is relatively minor and could be ignored in favor of simpler sampling strategies.

Figure 2A:
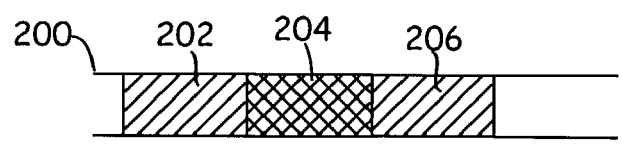
FIG. 2 schematically illustrates the interactions at an interface between fluid slugs in a microfluidic channel.
Figure 2B:
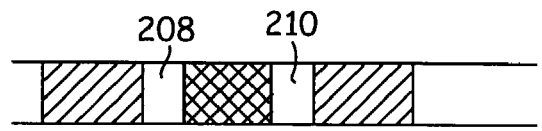

The specific interfacial interactions are schematically illustrated in FIGS. 2A and 2B. As shown, a first reagent plug 202 is introduced into the conduit 200. A second reagent 204 is introduced immediately adjacent to and bounded by the first reagent 202. A third reagent 206 is then introduced after and adjacent to the second reagent 204. The third reagent may be the same as or different from the first reagent 202. As shown in FIG. 2B, after a short period, the reagents 202, 204 and 206 diffuse and/or disperse into each other at their respective interfaces to form areas of reagent mixtures 208 and 210, respectively (illustrated by cross hatching). Thus, with the three reagent slugs 202, 204 and 206, potentially two different reactions are being carried out, e.g., within mixtures 208 and 210, if the first and third reagents represented two different reagents, or different concentrations of the same reagent. Further, as can be seen, the system includes a built in spacing fluid region in the form of the slug of the second reagent 204. By lining up slugs of different reagents, one can rapidly carry out a large number of different reactions, and particularly matrixed reactions, in a serial format.

The methods of the present invention are particularly useful in performing genotyping reactions on a relatively large number of patients with respect to a relatively large number of different genetic loci. By way of example, the first library of reagents consists of "patient specific" reagents, e.g., the genomic DNA from a number of different patients who are to be genotyped. The second library of reagents then consists of the "locus-specific" reagents, e.g., amplification primers for the subsequence that contains the particular locus of interest, as well as any other reagents specific to and necessary for discriminating the nature of the polymorphism at the locus, e.g., locus specific probes, i.e., nucleic acid or analog probes. Other reagents that are generic to the whole process are then included as part of one of the reagent libraries or are included in the system buffers, e.g., as part of each different library reagent plug, or are separately and continuously flowed into the conduit along with all of the different library reagents.

In the genotyping example, and with reference to FIG. 2, a first locus specific reagent mixture, e.g., primers and probes for amplifying a particular locus containing region of a patient's DNA, may be represented by reagent slug 202, while the template or patient DNA is contained in reagent slug 204. A second mixture of different locus specific reagents (specific for a different locus on the patient's DNA) would be represented by reagent slug 206. As each of the two different locus specific reagent mixtures diffuses and/or disperses into the patient specific reagent slug, e.g., containing the template DNA, the regions of overlap will be capable of supporting amplification of each of the two loci. Specifically, reagent mixture 208 would include the template DNA from slug 204, as well as the primers for amplifying the first locus containing region from slug 202, and any other locus specific reagents, e.g., locus specific probes that would be used for discrimination in certain processes. The second reagent mixture 210 would include the same template DNA, but primers (and optionally discrimination reagents, e.g., probes) that would be specific for the second locus. When the entire train of reagents, e.g., as shown in FIG. 2B is subjected to thermal cycling in the presence of a DNA polymerase and dNTPs, only the complete mixtures 208 and 210 would support amplification. Further, the amplified products would be distinguishable from each other by virtue of their physical isolation from each other.

Although described in terms of using discrimination reagents, e.g., nucleic acid probes that are specific for one variant or the other at a given locus, e.g., Molecular beacons or other signal generating probes, i.e., TaqMan probes, in certain preferred aspects, the discrimination is carried out by virtue of the use of an allele specific primer sequence used during amplification. A variety of different discrimination techniques are generally described in U.S. Patent Application No. 60/283,527, filed Apr. 12, 2001, the entire disclosure of which is incorporated herein by reference in its entirety for all purposes. Specifically, one of the primers is made to be sufficiently complementary to one variant of the polymorphic position in the template sequence, whereby the presence of the other variant will prevent hybridization and, consequently, amplification. In such case, no additional discrimination reagents are required, and detection is carried out by detecting whether amplification has occurred in the first instance. Such allele specific amplification is well known and is described in e.g., U.S. Pat. Nos. 5,525,494, 5,866,366, 6,090,552, and 6,117,635.

The interfacial mixing method allows all, or virtually all, of the reaction steps involved in performing the particular experiment, e.g., SNP genotyping, to be carried out in a single conduit for a large number of different patients and different loci. In particular, reagent mixing, amplification, discrimination and detection can all be carried out in this conduit while also including a built-in separation between the various experiments by virtue of the slugs of different reagents through which the other reagents have not completely diffused and/or dispersed. Stated in an alternative manner, one can screen an entire battery of reagents, e.g. locus specific reagents in a first reagent train where each of the locus specific reagent slugs is bounded by one patient specific reagent plug. The same battery can then be screened against another patient's DNA, by substituting a second patient specific reagent plug as the spacing reagent between the locus specific reagents.

The interfacial mixing methods of the present invention were demonstrated using two reagent slugs repeatedly and alternately introduced into a capillary channel. One of the reagent slugs included primers designed for amplification of a specific region of a template nucleic acid, a DNA polymerase, the four naturally occurring dNTPs, and a TaqMan probe that gave increasing fluorescence upon amplification of the specific region of the template. The other fluid contained the template nucleic acid. The contents of the capillary were subjected to thermal cycling through a temperature profile that supported melting of the template, annealing of the primers to the template and extension of those primers along the template.

Figure 3:
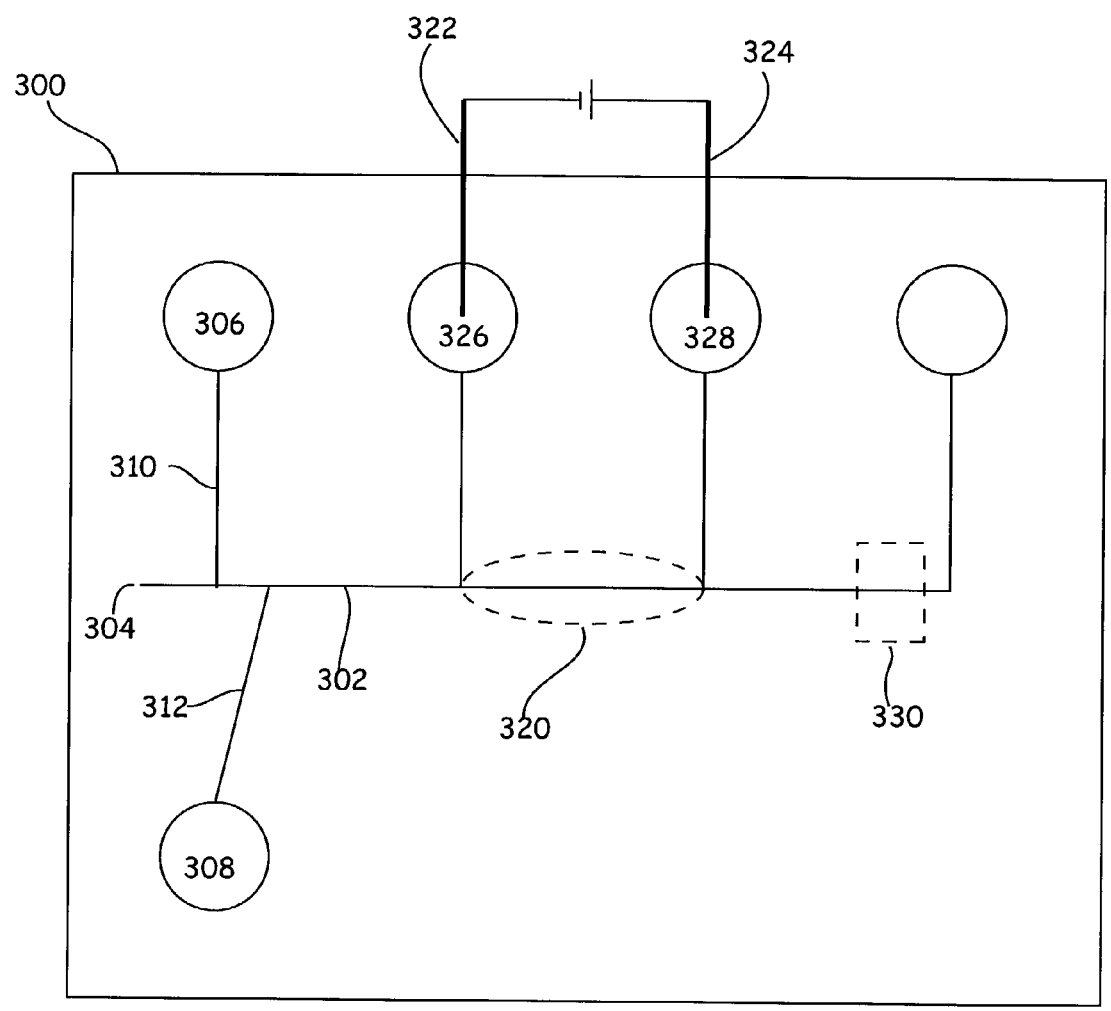
FIG. 3 schematically illustrates a channel network for use in carrying out the methods of the invention.

FIG. 3 schematically illustrates a microfluidic channel network useful in carrying out the methods of the invention. As shown, the channel network is disposed in a body structure of a microfluidic device 300. A sampling capillary (not shown) is attached to the body structure and used to sample reagents into the main channel 302 of the network, via port 304. The sampling capillary is placed into fluid communication with each of the different reagent source, in series, in order to serially introduce the different reagent slugs. Optional additional reagent sources 306 and 308 may be provided in the body structure 300, and in fluid communication with main channel 302, e.g., via channels 310 and 312, respectively. In the case of SNP genotyping experiments, it is generally desirable to include a heating zone 320 in main channel 302. The heating zone may be provided by placing an external or integral heating element, i.e., a resistive heater or peltier device, adjacent to or within the heating zone. Alternatively, electrical or "Joule heating" may be used to control the temperature of the heating zone 320. Controlled Joule heating is described in detail in U.S. Pat. No. 6,174,675. In the case of electrical heating, electrodes 322 and 324 are placed so as to be able to pass electrical current through the fluid in the heating zone 320 of main channel 302. As shown, such electrodes are placed in wells 326 and 328, respectively that are fluidly connected to main channel 302 at opposite ends of the heating zone 320. As will be appreciated, different applications may require multiple different heating zones, e.g., to heat to different temperatures, or for different uses, e.g., for generating thermal melting curves, etc. The electrodes are in turn, typically coupled to an appropriate electrical controller for providing current through the fluid in the heating zone in response to measured temperatures and desired temperature profiles. A detection zone 330 is also provided, which typically comprises a transparent region of the main channel 304, through which optical signals can be passed.

Figure 4:
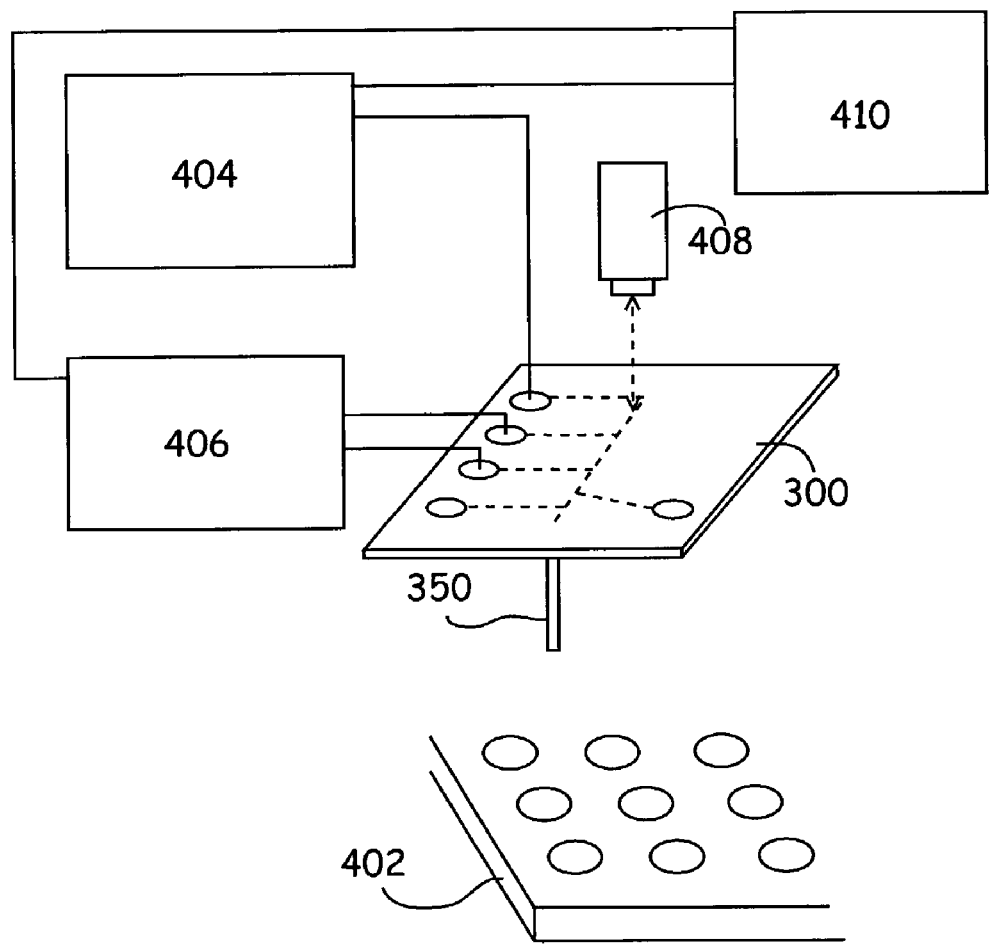
FIG. 4 schematically illustrates an overall system for use in carrying out the interfacial reactions of the present invention.

FIG. 4 schematically illustrates an overall system 400 for carrying out the methods of the invention. The system includes a microfluidic device 300 (shown as including external capillary element 350). The reagents are accessed through the capillary element 350 from source plates, e.g., multiwell plate 402. A flow controller 404 is also provided operably coupled to the microfluidic device 300, e.g., by a vacuum line, in the case of vacuum based flow, for driving fluid movement into and through the channels of device 300. Also shown is a temperature controller 406 operably coupled to the heating zone, for controlling and monitoring (either through an included sensor or via the monitoring of fluidic resistance, in the case of certain Joule heating embodiments) the temperature of the heating zone(s) in response to preprogrammed instructions from the user. As shown, the temperature controller is connected to the reservoirs of the device, as would be the case in Joule heating applications, although connection is similarly made to resistive heating elements attached to or disposed adjacent to the heating zone of the device. A detection system 408 is also typically included disposed within sensory communication of the main channel or channels of the microfluidic device, in order to detect the signal that is ultimately produced in the discrimination analysis. Typically, such detection systems include optical, and preferably, fluorescence detection systems that are well known in the art. In particular, in the case of genotyping experiments, a number of different discrimination techniques have been developed that produce a fluorescent signal that is indicative of one variant allele or the other, thus requiring fluorescence detection. Although illustrated as different units, it will be appreciated that the flow controller, temperature controller and detector may be integrated into a single instrument, for ease of use. A computer or other processor 410 is also typically included operably coupled to the various controllers and detectors of the system, in order to receive information from these system components, and instruct their operation in accordance with pre-programmed instructions.

Figure 5:
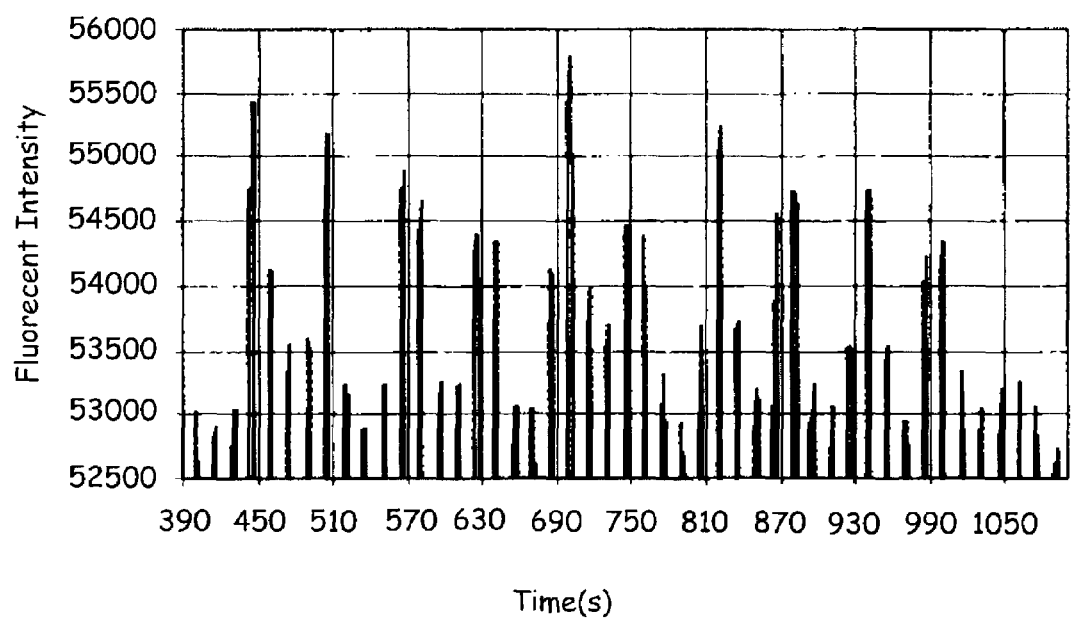
FIG. 5 shows results of PCR amplification reactions that are carried out in an interfacial format, in accordance with the present invention.

FIG. 5 is a plot of the fluorescent signal received from the capillary as the reagent slugs passed the detection point. The areas of increased fluorescence result from the fluorescent signal of a TaqMan probe that indicates amplification. As can be seen, amplification occurs only in regular spaced intervals that correspond to the regions surrounding the interface of the slugs of the two different reagents that were repeatedly interspersed into the capillary. Notably, the regions indicating amplification are separated by regions where no apparent amplification is taking place.

Although the present invention has been described in some detail by way of illustration and example for purposes of clarity and understanding, it will be apparent that certain changes and modifications may be practiced within the scope of the appended claims. All publications and patent applications referenced herein are hereby incorporated by reference to the same extent as if each individual publication or patent application was specifically and individually indicated to be incorporated by reference.

What is claimed is:

1. A method of analyzing a plurality of reactions, comprising:
   serially introducing plugs of first, second and third fluid borne reagents into a first fluid conduit under conditions suitable for performing the plurality of reactions whereby the plug of the first fluid borne reagent is abutted by the plug of the second fluid borne reagent at a first interface, and the plug of the second fluid borne reagent is abutted by the plug of the third fluid borne reagent at a second interface;
   allowing sufficient time for diffusion of effective amounts of the first and second reagents across the first interface whereupon the first and second reagents mix and react in a first reaction;
   allowing sufficient time for diffusion of effective amounts of the second and third reagents across the second interface, whereupon the second and third reagents react in a second reaction; and
   analyzing results of the first and second reactions.

2. The method of claim 1, wherein the plugs of first, second and third fluid borne reagents are being transported through the first fluid conduit.

3. The method of claim 1, wherein the second reagent comprises a target nucleic acid sequence, the first reagent comprises amplification reagents that are specific for a first portion of the target nucleic acid sequence, and the third reagent comprises amplification reagents that are specific for a second portion of the target nucleic acid sequence.

4. A method of performing a plurality of reactions, comprising:
   introducing a first volume of a first reagent into a fluid channel;
   introducing a first volume of a second reagent into the first fluid channel, the first volume of the second reagent abutting the first volume of the first reagent;
   introducing a first volume of a third reagent into the first fluid channel, the first volume of the third reagent abutting the first volume of the second reagent;
   diffusing the first and second reagents to diffuse together to form a first reaction in the first fluid channel;
   diffusing the second reagent and the third reagent together in the first fluid channel to form a second reaction mixture; and
   separately detecting a first reaction product in the first reaction mixture and a second reaction product in the second reaction mixture.

5. The method of claim 4, further comprising:
   introducing a second volume of the second reagent into the first fluid channel, the second volume abutting the first volume of the third reagent; and
   introducing a first volume of a fourth reagent into the first fluid channel, the first volume of the fourth reagent abutting the second volume of the second reagent;
   diffusing the fourth reagent and second reagent together to form a third reaction mixture; and
   detecting a reaction product in the third reaction mixture.

6. The method of claim 4, wherein the first reagent comprises a first locus specific reagent, the third reagent comprises a second locus specific reagent and the second reagent comprises a first patient specific reagent.

7. The method of claim 4, wherein the first reagent comprises a first patient specific reagent, the third reagent comprises a second patient specific reagent and the second reagent comprises a first locus specific reagent.

8. The method of claim 4, wherein the first volumes of the first, second and third reagents are flowing through the first fluid channel during the diffusing steps.

9. The method of claim 4, wherein the first fluid channel comprises at least one microscale cross-sectional dimension.

10. The method of claim 4, wherein the first fluid channel is fluidly connected to at least a second fluid channel.

11. The method of claim 4, further comprising mixing the first and second reaction mixtures with at least one other reagent prior to the detecting step.

* * * * *